United States Patent [19]
Kilmer et al.

[11] Patent Number: 5,395,385
[45] Date of Patent: * Mar. 7, 1995

[54] APPARATUS FOR SURGICALLY RE-PROFILING THE CORNEA

[75] Inventors: Lauren G. Kilmer; Alvin E. Reynolds, both of Tulsa, Okla.

[73] Assignee: Corneal Contouring, Inc., Azusa, Calif.

[ * ] Notice: The portion of the term of this patent subsequent to Nov. 29, 2011 has been disclaimed.

[21] Appl. No.: 979,424

[22] Filed: Nov. 19, 1992

Related U.S. Application Data

[60] Continuation of Ser. No. 762,898, Sep. 19, 1991, abandoned, which is a division of Ser. No. 450,672, Dec. 14, 1989, Pat. No. 5,063,942.

[51] Int. Cl.⁶ ............................................ A61F 9/00
[52] U.S. Cl. .................................. 606/166; 606/161; 606/180
[58] Field of Search ............... 606/166, 180, 161; 128/898, 757; 30/169, 172, 303, 347; 408/211, 223, 227, 228; 144/218, 219, 228, 229

[56] References Cited

U.S. PATENT DOCUMENTS

| | | | |
|---|---|---|---|
| 2,249,906 | 7/1941 | Longoria | 606/166 |
| 2,480,737 | 8/1949 | Jayle | 606/166 |
| 4,417,579 | 11/1983 | Soloviev et al. | 606/166 |
| 4,423,728 | 1/1984 | Lieberman | 606/166 |
| 4,515,157 | 5/1985 | Fedorov et al. | 606/166 |
| 4,526,171 | 7/1985 | Schachar | 606/166 |
| 4,619,259 | 10/1986 | Graybill et al. | 606/166 |
| 4,665,914 | 5/1987 | Tanne | 606/166 |
| 4,739,761 | 4/1988 | Grandon | 606/166 |
| 4,763,651 | 8/1988 | Kaufman et al. | 606/166 |
| 4,834,748 | 5/1989 | McDonald | 606/166 |
| 4,997,437 | 3/1991 | Grieshaber | 606/166 |

Primary Examiner—Michael H. Thaler
Attorney, Agent, or Firm—Head & Johnson

[57] ABSTRACT

Refractive error of the cornea is corrected by a scraping procedure of rotating or oscillating, about a center axis of the cornea, a sharpened knife edge blade that is tangential to and against that portion of the cornea to be corrected, and microaxially advanced until the refractive error has been corrected.

26 Claims, 6 Drawing Sheets

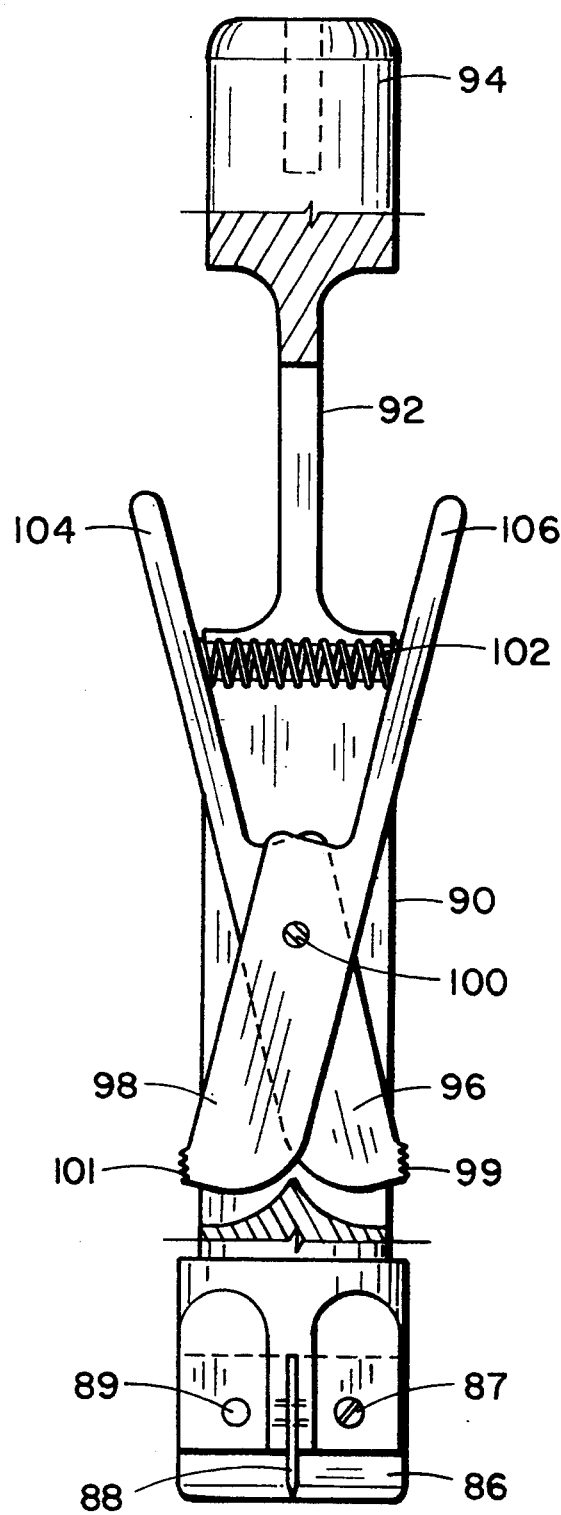
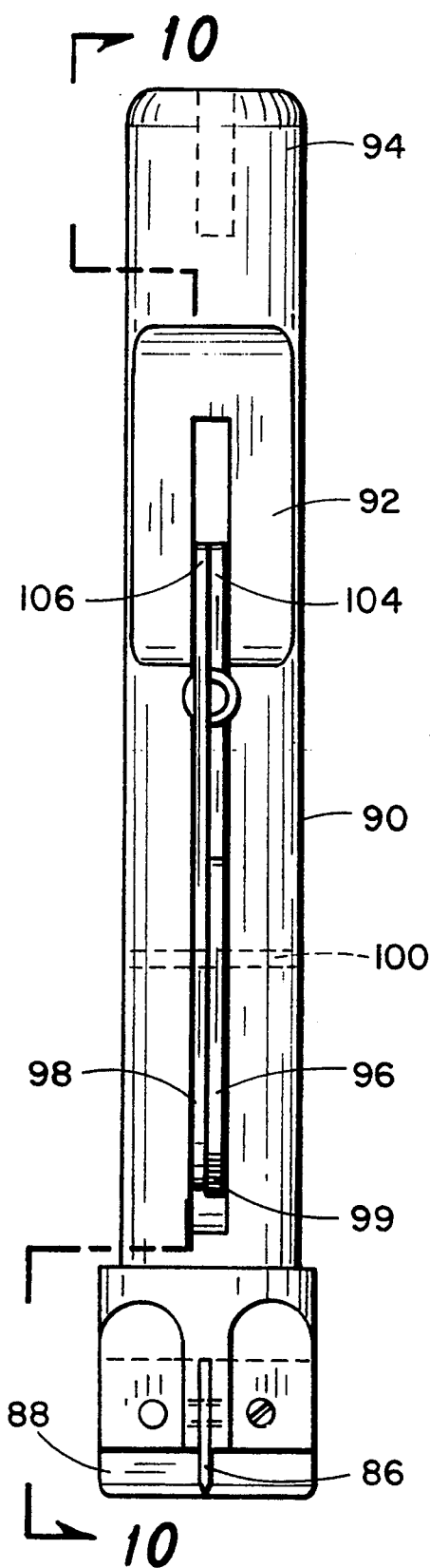
Fig. 10
Fig. 9

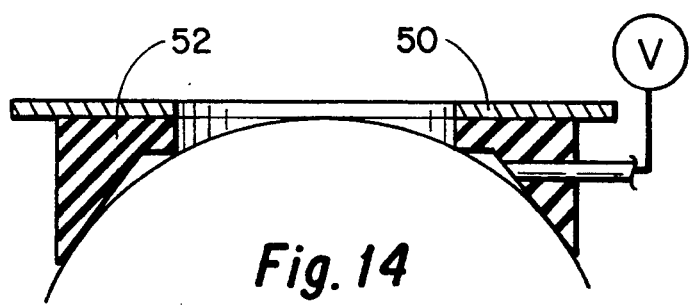
Fig. 14
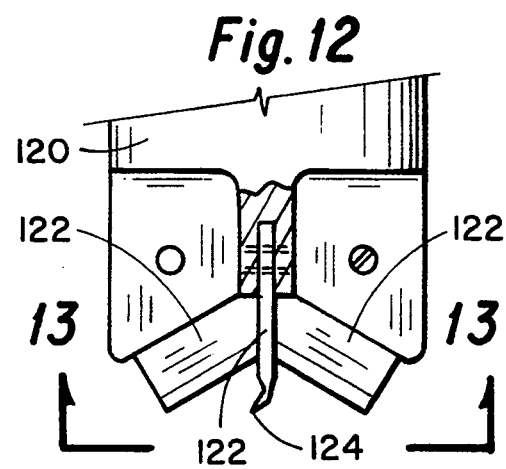
Fig. 12
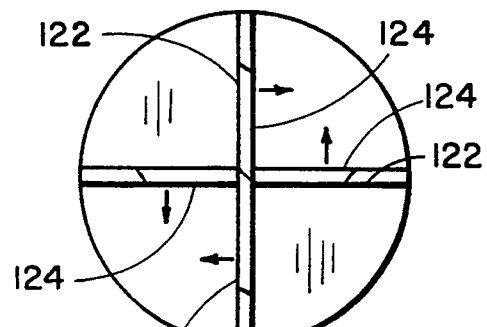
Fig. 13
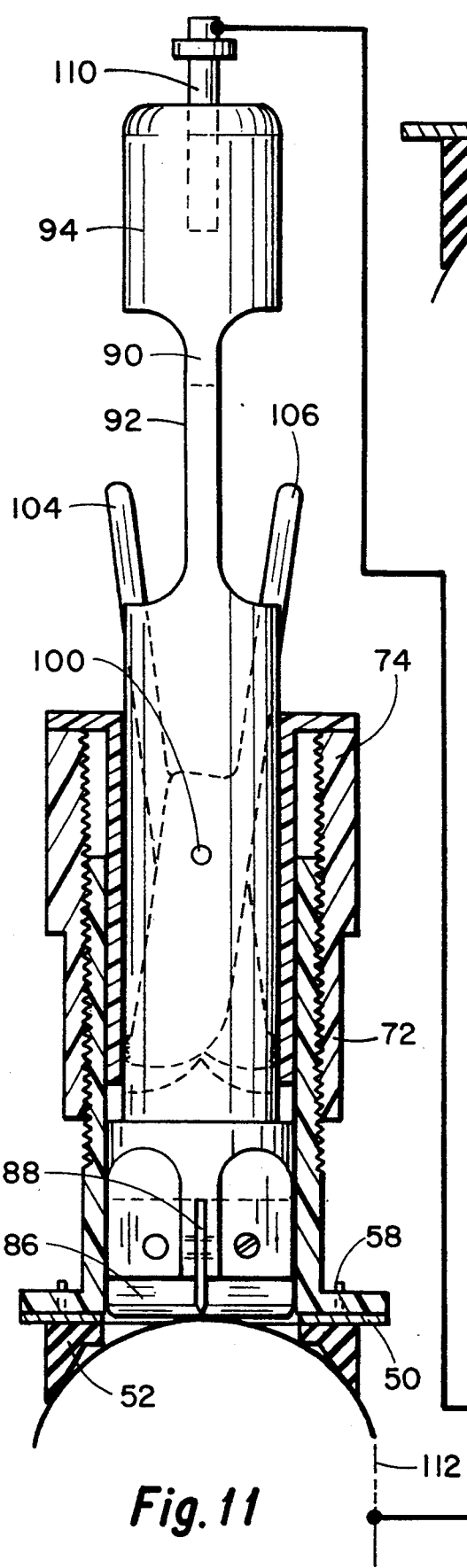
Fig. 11
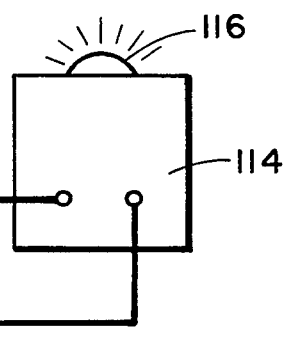

APPARATUS FOR SURGICALLY RE-PROFILING THE CORNEA

This is a continuation of application Ser. No. 07/762,898, filed on Sep. 19, 1991, now abandoned.

BACKGROUND OF THE INVENTION

This invention relates to a method and apparatus for adjusting the shape of components of the eye and more particularly to making fixed changes in the corneal curvature.

Deviations from the normal shape of the corneal surface produce errors of refraction in the visual process. The eye in a state of rest, without accommodation, focuses the image of distant objects exactly on the retina. Such an eye enjoys distinct vision for distant objects without effort. Any variation from this standard constitutes ametropia, a condition in which the eye at rest is unable to focus the image of a distant object on the retina. Hyperopia is an error of refraction in which, with the eye at rest, parallel rays from distant objects are brought to focus behind the retina. Divergent rays from near objects are focused still further back. In one aspect of hyperopia, the corneal surface is flattened which decreases the angle of refraction of rays as they pass through the refractive surfaces of the cornea, causing a convergence or focus of the rays at a point behind the retina. The retina is comprised partially of nerve fibers which are an expansion of the optic nerve. Waves of light falling on the retina are converted into nerve impulses and carried by the optic nerve to the brain to produce the sensation of light. To focus parallel rays on the retina, the hyperopic eye must either accommodate, i.e., increase the convexity of its lens, or a convex lens of sufficient strength to focus rays on the retina must be placed before the eye.

Myopia is that refractive condition in which, with accommodation completely relaxed, parallel rays are brought to focus in front of the retina. One condition which commonly causes myopia is when the corneal curvature is steepened, thus the refraction of rays is greater as they pass through the refractive surfaces of the cornea, and the over refracted rays converge or focus in front of the retina in the vitreous of the eye. When the rays reach the retina they become divergent, forming a circle of diffusion and consequently a blurred image. A concave lens is used to correct the focus of the eye for myopia.

The normal treatment of these classic forms of refractive error of the eye is with the use of eyeglasses or contact lenses, both of which have well-known disadvantages to the user. Recent research has been directed to operative techniques to change the refractive condition of the eye. Such techniques are generally referred to as "keratorefractive techniques". Two such techniques are more particularly called keratophakia and keratomileusis. Keralomileusis involves the regrinding of a corneal lamella into a meniscus or hyperopic lens to correct myopia or hyperopia. A corneal optical lathe has been especially developed for this procedure and is also used in the keratophakia procedure, when a homograft ground into a convex lens is placed interlamellarly to correct aphakic hypermetropia. The homograft tissue (corneal lamella) is frozen with carbon dioxide. The homograft is cut as a contact lens would be, i.e., to the optical power required to effect the desired optical correction of the cornea. In keratomileusis, the anterior corneal lamella is shaped by the lathe and in keratophobia, it is the corneal stroma of a donor eye that is shaped by the lathe. These techniques have a broad application in the correction of high hyperopic and myopic errors. These procedures require radial cutting of the cornea about the periphery of the graft which weakens the cornea so that pressure from fluids below the incisions pushes up under the cuts and flattens the curvature of the cornea. This flattening of the cornea results in refractive errors to the eye not compensated for by the graft. Suturing in these operations also causes radial asymmetry of the cornea which consequently promotes astigmatic error in this regard. Sutures also cause scarring of the corneal tissue, which scar tissue loses its transparency. Surgical correction of astigmatism is accomplished by asymmetrically altering the corneal curvatures. The effect of a peripheral distorting force may be easily visualized by imagining an inflated balloon with a spherical surface being compressed between the palms of the hands. Because the volume of air in the balloon is constant, the surface area remains constant. The previously spherical anterior surface is distorted meridianally as a result of compressing the diameter between the hands so that the curvature changes without changing the circumference of the surface. The meridian passing over the balloon between the extended fingers steepens, while the uncompressed meridian at right angles thereto flattens as its diameter lengthens in proportion to the shortening of the compressed diameter. This demonstrates the effect that may result from slight variations in the symmetrical patterns or intentional asymmetrical patterns attempted to be accomplished during surgical procedures and attendance suturing. It is thus seen that present procedures in keratorefractive techniques are best limited to situations where other more standard corrective practices are found in effective. It is readily seen that the limiting factors in such surgical techniques is the gross complexity involved not only with multiple incisions in corneal tissue for affecting the procedures but also complex suturing patterns, resulting in gross restructuring of the eye. The eye is thus faced with a difficult job of adjusting to this trauma.

Over the past few years developments have been made in the use of lasers as a means to reshape the cornea in an attempt to get rid of refractive errors. In these processes, pulsed lasers remove tissue from the cornea, the most common type being an Exemer laser. The fundamental effect of such a laser on tissue is a-photochemical one, the breaking of molecular bonds with so much energy that the tissue fragments fly fro the surface at supersonic speeds, leaving behind a discreet space. The process has been designated as ablative photodecomposition or photoablation.

The use of Exemer lasers require delivery of the beam to the eye in a controlled manner requiring that the homogenous beam be appropriately managed and focused because the optical elements must withstand the high energy photons, and because the beam must be shaped to a non-uniform configuration to create the new non-uniform optical surface of the cornea. Such delivery system contains multiple components including lenses to expand or focus the beam, mirrors to direct the beam, modulators to homogenize the beam, masks to shape the beam, and detectors to measure the intensity and configuration of the beam. Current models range from a simple collection of lenses and masks to complex robots with components that control not only the laser parameters but also the optical and mechanical components. Because the process is dealing with submicron (less than 0.000001 of a meter) accuracy, great demands are placed upon such systems for stability, even thought he interaction of the laser and tissue lasts only microseconds.

Using the system requires exquisite technical and biological control to modulate corneal wound healing.

SUMMARY OF THE INVENTION

It is therefore an object of the present invention to provide a new and improved keratorefractive technique involving method and apparatus for changing the shape of the optical zone of the cornea to correct refractive errors of hyperopia (far-sightedness), myopia (near-sightedness), and astigmatism, whereby a minimum disturbance is imposed on the eye system and the simplicity of the technique virtually eliminates the chance of error or further complications resulting from gross disturbances of the eye system.

With this and other objects in view, the present invention contemplates a method and apparatus for sculpting or scarifying the cornea for the purposes of correcting refractive error.

Another object of the invention is to provide mechanical apparatus capable of easily being used by a surgeon for sculpting or scarifying the cornea in order to correct for hyperopia, myopia, and astigmatism which includes means to provide consistency in depth and configuration of the surface.

Specifically, the method objects of this invention involve the surgical reprofiling of the corneal portion of the eye to change the corneal radius and thus correct refractive errors. The steps include creating a placido ring keratograph of a simulated cornea having the correct refractive qualities. Next, an actual keratograph of said cornea is created. The two kerotographs are compared to determine the amount of refractive error, i.e., whether it would be hyperopia, myopia, or astigmatism. A profiling tool is constructed that includes a plurality of incising blades of shape sufficient to sculpt the cornea and thus change its corneal radius to that of the simulated cornea. The profiling tool is then positioned within a holding sleeve that is contiguously positioned upon said eye such that the incising blades will contact the cornea. The profiling tool is then rotated or oscillated until the corneal radius has been corrected to that of the simulated cornea. The profiling tool includes means for making precise axial depth changes as needed during the operational procedures.

The apparatus used to achieve the objects of this invention specifically includes a circular positioning ring having a resilient vacuum ring means on its bottom side for temporary attachment to the sclera portion of an eye which surrounds the cornea that is to be reprofiled. A plurality of positioning pins exist on the top side of the positioning ring and a vacuum means is provided for communication with the vacuum ring. A cylindrical holding sleeve includes means at the bottom of the holding sleeve to interconnect with the pins of the circular positioning ring. Fine Screw threads of a given pitch, preferably about 40 threads per inch, are formed on the exterior portion of the holding sleeve. Threadably connected thereto is a guide sleeve having screw threads of the same pitch which are formed interiorly thereof for rotatable attachment with the holding sleeve. A profiling tool is adapted to be rotatably and axially received within the positioning ring, the holding sleeve, and the guide sleeve. A collar means existing on the profiling tool allows it to be rotatably supported upon the guide sleeve. A plurality of scarifying blades at the bottom of the profiling tool are designed to be of a shape sufficient to sculpt or form the desired corrective curvature in the corneal portion.

Another object of the invention is to provide a means to incise, sculpt, and scarify the outer anterior surface of a cornea to reprofile same to correct for refractive error, and to do so with a minimum or no inflammation and with regrowth of the epithelium layer of the cornea in a minimum amount of time.

Another object is to achieve a reprofiled cornea, as set forth in the previous object, that will permit regrowth of the epithelium layer from unshaped areas of the cornea, without returning to the original curvature.

BRIEF DESCRIPTION OF THE DRAWINGS

FIG. 9 is a side elevational view of an alternate scarifying tool.

FIG. 10 is a front sectional view taken along the line 10—10 of FIG. 9.

FIG. 11 is an assembly view of the apparatus of the invention with an electrical indicating means.

FIG. 12 is a partial sectional view of an alternate embodiment.

FIG. 13 is an end elevationalal view taken along line 13—13 of FIG. 12.

FIG. 14 is an enlarged partial sectional view of the positioning ring on an eye.

DETAILED DESCRIPTION OF THE PREFERRED EMBODIMENT

Before explaining the present invention in detail, it is to be understood that the invention is not limited in its application to the details of the construction and arrangement of parts illustrated in the accompanying drawings. The invention is capable of other embodiments and of being practiced or carried out in a variety of ways. It is to be understood that the phraseology and terminology employed herein is for the purpose of description and not of limitation.

Figure 1:
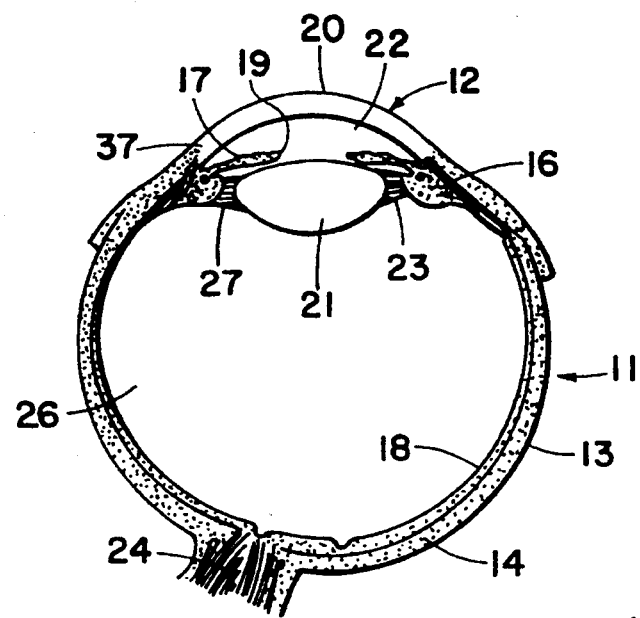
FIG. 1 is a schematic illustration of a horizontal section of the eye.

Referring first to FIG. 1 of the drawings, a horizontal section of the eye shows the globe of the eye resembling a sphere with an anterior bulged spherical portion 12 representing the cornea. Thus the eye is actually comprised of two somewhat modified spheres placed one in front of the other. The anterior of these two segments is the smaller more curved cornea.

The globe of the eye consists of three concentric coverings enclosing the various transparent media through which the light must pass before reaching the sensitive retina. The outermost covering is a fibrous protective portion, the posterior five-sixths of which is white and opaque and called the sclera 13, and sometimes referred to as the white of the eye where visible to the front. The anterior one-sixth of this outer layer is the transparent cornea 12.

A middle covering is mainly vascular and nutritive in function and is comprised of the choroid 14, ciliary body 15 and iris 17. The choroid generally functions to maintain the retina. The ciliary muscle is involved in suspending the lens and accommodation of the lens. The iris is the most anterior portion of the middle covering of the eye and is arranged in a frontal plane. It is a thin circular disc corresponding to the diaphragm of a camera, and is perforated near its center by a circular aperture called the pupil 19. The size of the pupil varies to regulate the amount of light which reaches the retina. It contracts also to accommodation, which serves to sharpen the focus by diminishing spherical aberration. The iris divides the space between the cornea 12 and the lens 21 into an anterior chamber 22 and posterior chamber 23. The innermost portion of covering is the retina 18, consisting of nerve elements which form the true receptive portion for visual impressions.

The retina is a part of the brain arising as an outgrowth from the fore-brain, with the optic nerve 24 serving as a fibre tract connecting the retina part of the brain with the fore-brain. A layer of rods and cones, lying just beneath a pigmented epithelium on the anterior wall of the retina, serve as visual cells or photoreceptors which transform physical energy (light) into nerve impulses.

The vitreous 26 is a transparent gelatinous mass which fills the posterior four-fifths of the globe. At its sides it supports the ciliary body 16 and the retina 18. A frontal saucer-shaped depression houses the lens 21.

The lens 21 of the eye is a transparent bi-convex body of crystalline appearance placed between the iris 17 and vitreous 26. Its axial diameter varies markedly with accommodation. A ciliary zonule 27, consisting of transparent fibers passing between the ciliary body 16 and lens 21 serves to hold the lens in position and enable the ciliary muscle to act on it.

Referring again to the cornea 12, this outermost fibrous transparent coating resembles a watch glass. Its curvature is somewhat greater than the rest of the globe and is ideally spherical in nature. However, often it is more curved in one meridian than another giving rise to astigmatism. A central third of the cornea is called the optical zone with a slight flattening taking place outwardly thereof as the cornea thickens towards it periphery. Most of the refraction of the eye takes place on the surface of the cornea.

Figure 2:
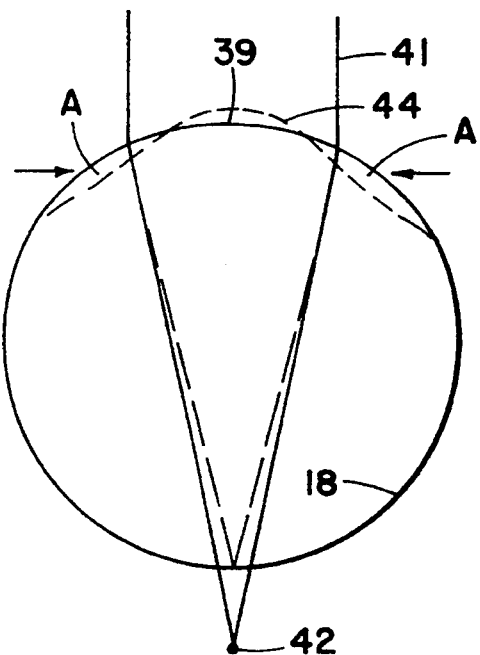
FIG. 2 is a schematic illustration of a hyperopic eye showing adjustment of the cornea to shorten the radius of curvature.

Referring next to FIG. 2 of the drawings, the globe of an eye is shown having a cornea 12 with a normal curvature represented by the solid line 39. If parallel rays of light 41 pass through the corneal surface 39 of FIG. 2, they are refracted by the corneal surfaces to converge eventually near the retina 18 of the eye. The diagram of FIG. 2 discounts, for the purposes of this discussion, the refractive effect of the lens or other portions of the eye. The eye depicted in FIG. 2 is hyperopic and thus the rays of light 41 are refracted to converge at point 42 behind the retina. If a peripheral band of pressure is applied inwardly at the chord 43 of the cornea, the walls of the cornea are caused to steepen. This is because the volume of fluids within the anterior chamber 22 remains constant, thus the anterior portion of the cornea, including the optical zone (inner third of the cornea) steepens in slope to form a curvature (shown in exaggeration) following the dotted line 44. The rays of light 41 are then refracted from the steeper surface 44 at a greater angle to direct the refracted rays into focus at a shorter distance, such as directly on the retina 18.

Figure 3:
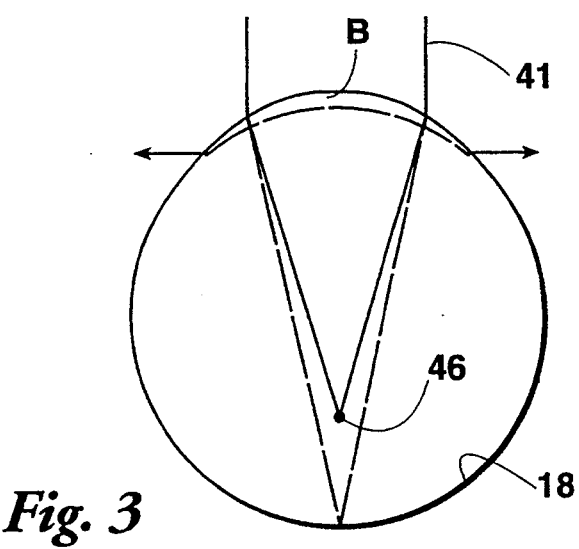
FIG. 3 is a schematic illustration of a myopic eye system showing adjustment of the cornea to increase its radius and thus flatten the corneal slope.

FIG. 3 shows a similar eye system to that of FIG. 2 except that the so-called normal corneal curvature of FIG. 3 causes the light rays 41 to refract into focus at a point 46 in the vitreous which is short of the retinal surface 18. This is typical of a myopic eye. If chord 43 of the cornea is expanded uniformly outwardly as shown by the arrows, the walls of the cornea are flattened. Light rays 41 refracted by the now flattened corneal surface will be refracted at a smaller angle and thus converge at a more distant point such as directly on the retina 18.

Figure 4:
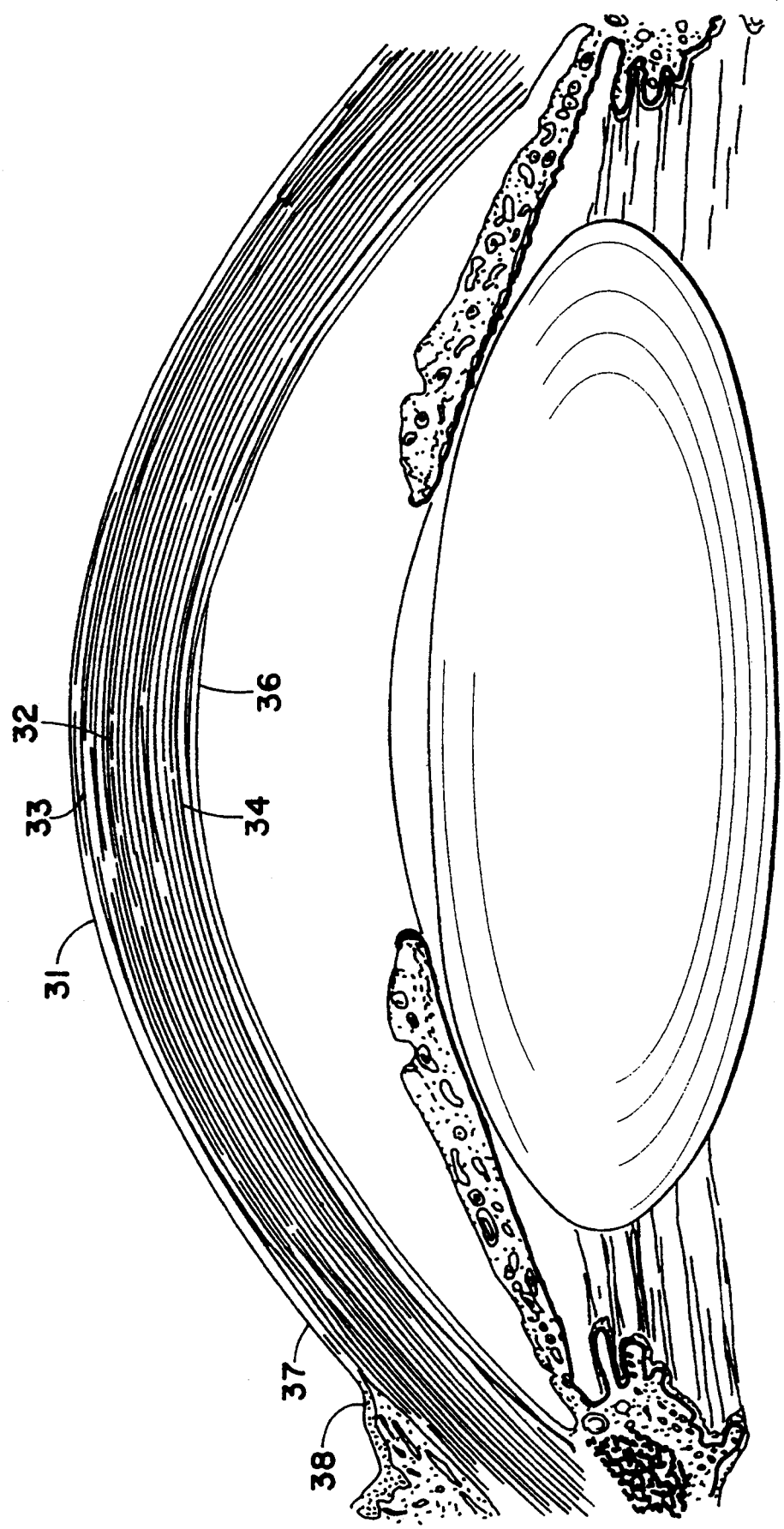
FIG. 4 is a detailed schematic illustration of a horizontal section of the frontal portion of an eye showing the various layers of the cornea.

Referring now to FIG. 4, a more detailed drawing of the anterior portion of the globe shows the various layers of the cornea comprising an epithelium 31. Epithelial cells on the surface thereof function to maintain transparency of the cornea. These epithelial cells are rich in glycogen, enzymes and acetylcholine and their activity regulates the corneal corpuscles and controls the transport of water and electrolytes through the lamellae of the stroma 32 of the cornea.

An anterior limiting lamina 33, referred to as Bowman's membrane, is positioned between the epithelium 31 and the substantia propria or stroma 32 of the cornea. The stroma is comprised of lamella having bands of fibrils parallel to each other and crossing the whole of the cornea. While most of the fibrous bands are parallel to the surface, some are oblique, especially anteriorly. The fibrous bands within alternate lamella are at a near right angle to bands in the adjacent lamella. A posterior limiting lamina 34 is referred to as Descemet's membrane. It is a strong membrane sharply defined from the stroma and resistant to pathological processes of the cornea.

The endothelium 36 is the most posterior layer of the cornea and consists of a single layer of cells. The limbus 37 is the transition zone between the conjunctiva 38 and sclera 13 on the one hand and the cornea 12 on the other.

Figure 5:
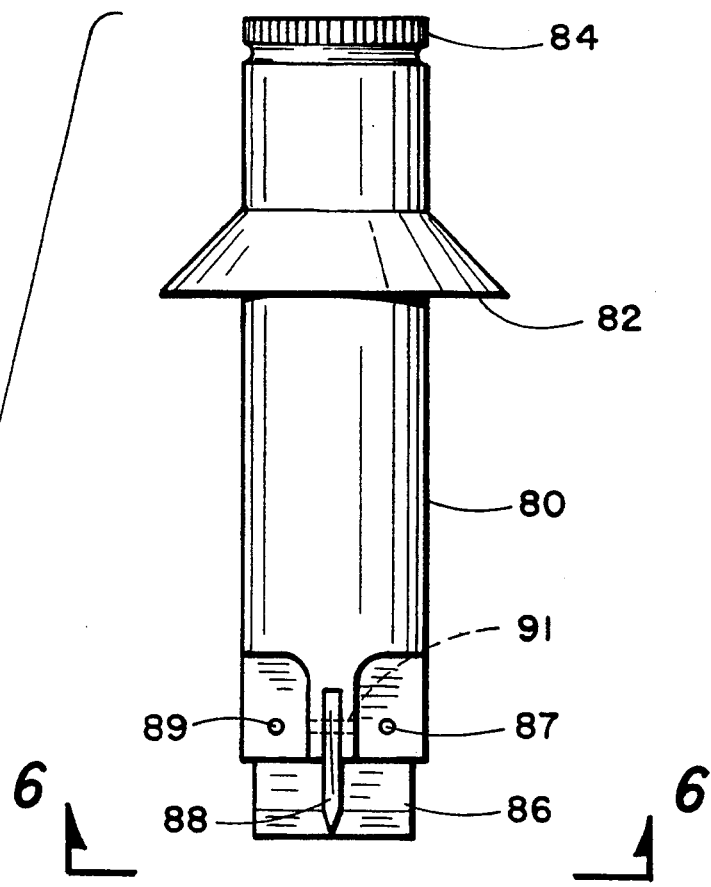
FIG. 5 is an exploded view showing the basic components of the apparatus of this invention.
Figure 5:
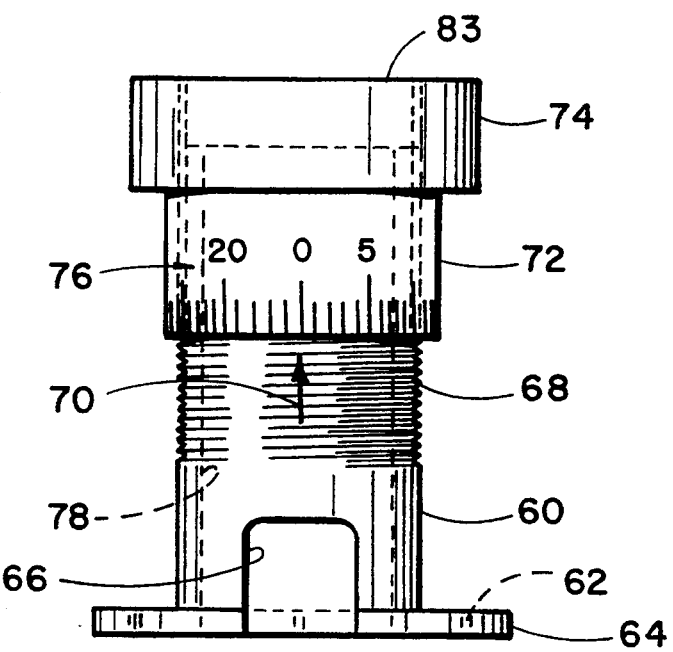
Figure 5:
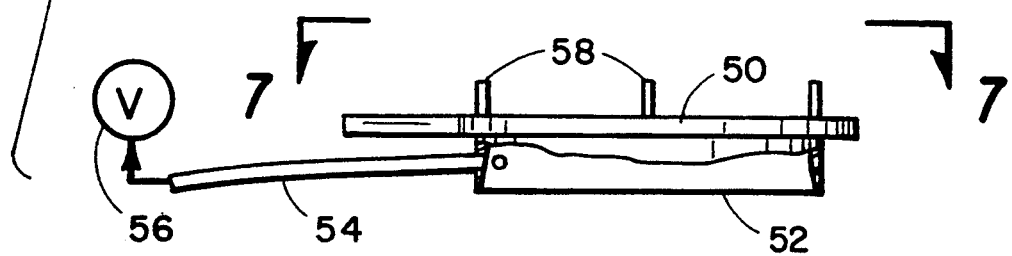
Figure 6:
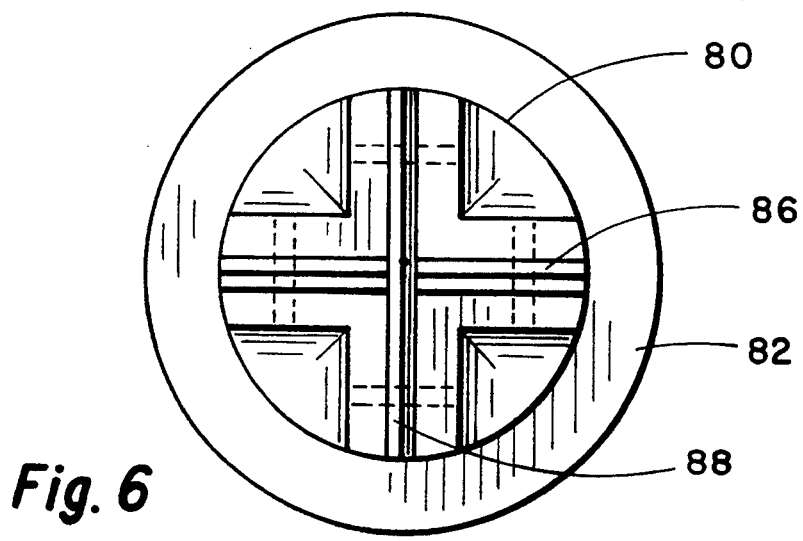
FIG. 6 is a bottom end elevational view of the profiling tool taken along the line 6—6 of FIG. 5.
Figure 7:
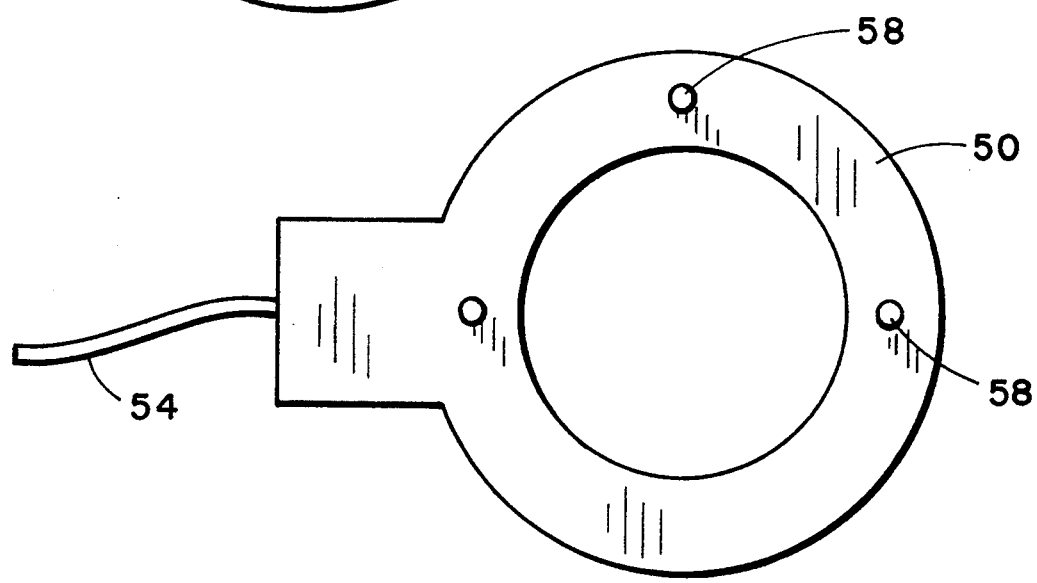
FIG. 7 is a top elevational view of the positioning ring of the invention.

Referring now to FIG. 5 wherein the assembly of the basic parts of the apparatus are shown in an exploded view. These parts comprises a cylindrical positioning ring 50 having a resilient vacuum ring 52 extending from the bottom side of the positioning ring for contact with the eye of the patient being treated. A vacuum hose 54 provides communication from the inside of the resilient ring 52 and a vacuum pump source means 56 as a means to retain the assembled parts upon the eye for surgical procedures herein described and to remove scarified portion of the cornea. A plurality of positioning pins 58 are provided on the top side of the positioning ring to receive the cylindrical holding sleeve 60, the pins being adapted to be received through openings 62 in the flange portion 64. A visual inspection opening 66 is provided for use by the surgeon. The exterior of the cylindrical holding sleeve 60 includes a plurality of screw threads 68 along its length, the threads being a very fine pitch thread, e.g., of a pitch equal to 40 threads per inch. An indicia or marker 70 is provided in the body of the cylindrical holding sleeve so as to provide a visual measuring point for the surgeon relative to the rotatable position of a micrometer-like guide sleeve 72 which includes interior threads to match threads 68 of the cylindrical holding sleeve. The guide sleeve includes an outer knob portion 74 and indicia generally designated by the numeral 76, e.g. millimeter or micrometer like markings on the lower portion of the guide sleeve. The interior 78 of the cylindrical holding sleeve is adapted to rotatably receive a profiling tool 80. The profiling tool includes a collar 82 which is adapted to rest upon the top surface 83 of the guide sleeve 72 for movement upwardly or downwardly therewith. The top end of the profiling tool can include a knurled portion 84 for rotation and/or oscillation by the surgeon. At the bottom of the profiling tool are a plurality of scarifying surgically sharp knife-edge blades 86 and 88 which are retained within the body of the profiling tool 80 by pins 87, 89 and 91. The blades 86 and 88 are retained transverse to the longitudinal axis of the profiling tool 80. The blades 86 and 88 as used in the invention are of surgical steel.

The profiling tool 80 of FIG. 5 is adapted to provide a scarifying or sculpting operation upon the cornea over the top center thereof for myopia refractive error, i.e., nearsightedness, which will effectively lengthen the corneal radius of curvature as shown in FIG. 3.

Figure 8:
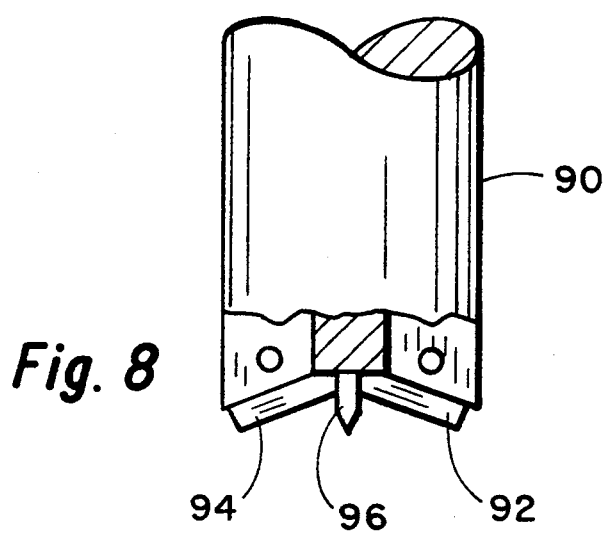
FIG. 8 is a partial sectional view of an alternate profiling tool.

To correct for hyperopia (far-sightedness), the profiling tool as shown in FIG. 8 is utilized, the tool having a shank 90 of similar design to tool 80 shown in FIG. 5, except that the bottom end of the tool includes a plurality of surgical steel knife-edge blades 92, 94 and 96 which are positioned transverse to the axis of the tool at an angle of approximately 30° with respect to the horizontal axis (or 60° to the vertical axis). The blades are adapted to contact the outer anterior portion of the cornea in order to shorten the effective radius thereof, that is, the blades will be adapted to contact and scarify the corneal area A as shown in FIG. 2 whereas the profiling tool 80 of FIG. 5 will be adapted to sculpt or scarify the area B of FIG. 3.

OPERATION

The operation of the apparatus and methods of surgery are accomplished by first taking optical measurements of the eye as to what shape the cornea should have in order for that eye to operate in an optically correct manner, i.e., correct refractive errors. Typically, a kerotograph photographic image using a placido-ring target is used. The photograph is of reflected light from the placido rings upon a standard spherical surface of the same size as the cornea in question, creating an image in the same manner as a topographic contour map. Subsequently, the topographic survey of the eye to be corrected is made for comparison purposes and to provide the surgeon with the necessary dioptic information for correcting the refractive errors. Once this occurs, then the operation will proceed by placing the positioning ring 50 over the eye as shown in FIG. 14. The size of this ring may vary for different operations but is preferably of size wherein the resilient vacuum ring 52 will rest upon the sclera portion of the eye concentric about the cornea. Once the circular positioning ring 50 is in place, the cylindrical holding sleeve 60 is then positioned thereupon by the engagement of openings 62 with positioning pins 58. The profiling tool 80 is then inserted within the cylindrical holding sleeve 60 to a position where the bottom of the knife-edge blades 86 and 88 will initially contact the cornea. By rotating the guide sleeves 72 in incremental amounts as dictated by the caliper or measuring scales 70 and 76, the surgeon can continue to increase the depth of the sculpting operation. The scarifying or sculpting of the cornea occurs by hand rotation or reciprocation of the profiling tool 80 although other mechanical or motor operated means are within the scope of this invention.

In myopic conditions, the profiling tool 80 of FIG. 5 is utilized. During the operation, the knife-edge blades press upon the corneal surface which becomes depressed and thus gives a larger contact surface with the blades resulting in a larger diameter of sculptured surface. The scarifying or sculpting action is accentuated in proportion to the pressure between the cornea and the blade. The resulting effect is a lengthening of the refractive radius in that portion of the cornea under the blade. When the tool is removed, the cornea returns to its normal contour except that the radius over the top center thereof is now longer than it was initially. As a result, refractive light through the cornea now focuses upon the retina. The scarifying action occurs by the surgeon in incremental movement by rotating or reciprocating the guide sleeve 72 relative to cylindrical holding sleeve 60 utilizing the incremental measuring indicia 76 relative to a pointer or other indicia 70. Typically, the guide sleeve is graduated into 25 or 50 micrometer divisions to provide one hundredth millimeter adjustments for each marked division of rotation. Through use, the surgeon begins to decide the amount of downward movement needed to achieve the required changes in the cornea by the rotation and/or oscillation of the knives. The rotation for a period of a few seconds will result in removal of small amounts of corneal material from the cornea. The tool can be removed and/or kerotographic photographs taken to determine if the refractive error has been corrected. Since the apparatus and the surgical methods deal with very small increments of movement in the corneal reprofiling process, it is essential that the first contact setting be precise and accurate. Many times this can be done by visual means by the surgeon and in other instances electrical detecting means can be provided between the cornea and the tool blade to provide an exact setting of the tool which permits repeatable amounts of corneal removal.

The profiling tool of FIGS. 9 and 10 represent a modified form comprising a body 90 with an indented handle 92 and a knurled finger knob 94. In this embodiment an internal sleeve clamp is comprised of scissor elements 96 and 98 which are pivoted at pin 100. The outer ends of the elements are grooved at 99 and 101 to provide a gripping action against the internal diameter of the tool guide or holding sleeve 60. A spring 102 normally biases the blade handles 104 and 106 outward. Pinching the handles 104 and 106 inward retracts respective elements 96 and 98 so as to be able to be inserted into the cylindrical holding sleeve 60. Release of the handles causes the elements 96 and 98 to frictionally engage with the internal periphery of sleeve 60.

FIG. 11 provides an electrical indication means for the surgeon to determine the initial contact of the tool blades. A first contact electrode 110 is removably connected with the conductive tool 90. A second electrode is grounded to the patient at 112. The leads are connected to a low voltage power source 114 including an indicator lamp 116. Once the blade touches the cornea, the light will go on which provides the initial contact point from which downward movement measurements begin. Typically a predetermined amount of corneal material is set into the tool by rotating the guide tool 72 downwardly. The rotation or oscillation of the profiling tool 80 then begins to change the contour of the cornea. Measurements are then taken to determine if more corneal material removal is necessary. If so, a new depth is set, and the process is repeated. The profiling tool is designed to be removed and replaced without changing the depth setting of the sleeve 72. Typically the amount of depth removal is about two thousandths of an inch (0.002"). Many times it is necesary to operate in several cycles with measurements being taken after each cycle. A nomogram used with a computer generated set of curves of the cornea before and after each contouring procedure permits the surgeon to constantly monitor the amount of removal of the epithelium layer and/or in some cases portions of Bowman's layer. It has been found that the epithelium will return over the surface of the contoured portion in a period of 24 to 48 hours. However, there will be no regrowth of the Bowman's laywer which will cause the changed radius to remain. The epithelium will return and regrow to its same thickness and clarity but with a changed radius.

TEST EXAMPLES

A series of tests have been made upon rabbit eyes and have resulted in uniform repeatable changes in corneal shape.

In these experiments the apparatus of FIG. 5 and the profiling tool of FIG. 8 were utilized. The rabbits were anesthetized and the procedure above described was performed to the cornea of the animals. The following chart describes the results of the corneal changes in terms of the amount of pre and post corneal curvature change relative to the depth of the cutter setting:

| CORNEA NO. | RADIUS MM PRE-CURVE | POST-CURVE | BLADE-DEPTH |
| --- | --- | --- | --- |
| 1 | 7.05 | 7.70 | .002" |
| 2 | 7.40 | 7.90 | .002" |
| 3 | 8.00 | 8.70 | .002" |
| 4 | 8.00 | 8.60 | .001" |
| 5 | 7.22 | 7.70 | .001" |
| 6 | 7.10 | 7.60 | .001" |

FIGS. 12 and 13 represent a modified form of profiling tool blade design, shown here for correcting hyperopia, but the same concept is applicable to myopia correcting tools. The body 120 includes a plurality of radially intersecting blades 122. The extreme tip 124 of the sharpened end of each blade is bent at an angle preferably of 120°. The bend of the edge of the blades are in alternate directions as shown by the arrows in FIG. 13.

FIG. 14 is an enlarged view of the positioning ring 52 as positioned on an eye forming a small vacuum pocket for maintaining the ring on the eye during surgery.

What is claimed is:

1. Apparatus for surgically reprofiling the corneal portion of an eye of a human to change the corneal radius and thus correct refractive errors, comprising a cylindrical positioning ring having resilient vacuum means on its bottom side for temporary attachment to a sclera portion of said eye and surrounding said cornea to be reprofiled, and vacuum means communicating with said vacuum ring means:

a holding sleeve, means at a bottom of said holding sleeve to interconnect with said positioning ring, screw threads of a given pitch formed on an exterior portion of said holding sleeve, a guide sleeve having screw threads of said given pitch formed interiorly thereof for rotatable attachment with said screw threads of said holding sleeve;

a profiling tool, said profiling tool adapted to be rotatably and axially received within said holding sleeve and said guide sleeve, a collar means on said profiling tool to rotatably support said profiling tool upon said guide sleeve, at least one sharpened knife edge blade at the bottom of said profiling tool; and means to rotate or oscillate said knife edge relative to a visual axis of said eye so as to scrape said cornea until said refractive error has been substantially corrected.

2. Apparatus of claim 1 wherein said knife edge blade is such to effectively increase the corneal radius.

3. Apparatus of claim 1 wherein said knife edge blade is such to effectively decrease the corneal radius.

4. Apparatus of claim 1 wherein said holding sleeve is substantially transparent.

5. Apparatus of claim 1 wherein said pitch of said screw threads is between 35 to 50 threads per inch.

6. Apparatus of claim 5 wherein said pitch of said screw threads is 40 threads per inch.

7. Apparatus of claim 6 wherein said holding sleeve and said guide sleeve includes micrometer indexing means for measuring the axial movement of said profiling tool.

8. Apparatus of claim 1 including a first electrical contact connected to said profiling tool, a second electrical contact connected to said human, and an on-off electrical power circuit means connecting said first and second contacts with a visual and/or audible indicator means of an initial contact of said knife edge blade with said cornea.

9. Apparatus of claim 1 wherein said profiling tool includes frictional means releasably engageable with the inner periphery of said holding sleeve.

10. Apparatus of claim 7 wherein said holding sleeve and said guide sleeve include micrometer indexing means for measuring axial movement of said profiling tool.

11. Apparatus for surgically reprofiling the corneal portion of an eye of a human to change the corneal radius and thus correct refractive errors, comprising a cylindrical positioning ring having resilient vacuum means on its bottom side for temporary attachment to a sclera portion of said eye and surrounding said cornea to be reprofiled, and vacuum means communicating with said vacuum ring means:

a holding sleeve, means at a bottom of said holding sleeve to interconnect with said positioning ring, screw threads of a given pitch formed on an exterior portion of said holding sleeve, a guide sleeve having screw threads of said given pitch formed interiorly thereof for rotatable attachment with said screw threads of said holding sleeve;

a profiling tool, said profiling tool adapted to be rotatably and axially received within said holding sleeve and said guide sleeve, a collar means on said profiling tool to rotatably support said profiling tool upon said guide sleeve, a plurality of radial blades at the bottom of said profiling tool, the bottom sharpened knife edges of which are transverse to the axis of said profiling tool; and means to rotate or oscillate said knife edge relative to a visual axis of said eye so as to scrape said cornea until said refractive error has been substantially corrected.

12. Apparatus for surgically reprofiling the corneal portion of an eye of a human to change the corneal radius and thus correct refractive errors, comprising a cylindrical positioning ring having resilient vacuum means on its bottom side for temporary attachment to a sclera portion of said eye and surrounding said cornea to be reprofiled, and vacuum means communicating with said vacuum ring means:

a holding sleeve, means at a bottom of said holding sleeve to interconnect with said positioning ring, screw threads of a given pitch formed on an exterior portion of said holding sleeve, a guide sleeve having screw threads of said given pitch formed interiorly thereof for rotatable attachment with said screw threads of said holding sleeve;

a profiling tool, said profiling tool adapted to be rotatably and axially received within said holding sleeve and said guide sleeve, a collar means on said profiling tool to rotatably support said profiling tool upon said guide sleeve, a plurality of radial blades, at the bottom of said profiling tool, the bottom sharpened ends of which are concave relative to the axis of said profiling tool, to effectively increase the corneal radius; and means to rotate or oscillate said knife edge relative to a visual axis of said eye so as to scrape said cornea until said refractive error has been substantially corrected.

13. Apparatus for correcting refractive error in an eye having a cornea with a center visual axis, comprising:

a profiling tool, said tool having a sharpened straight knife edge blade of shape to incise said cornea to said desired corneal radius;

means co-axial to said visual axis to receive and support said profiling tool such that said blade is tangential to and against a top of said cornea at its center axis; and means to rotate or oscillate said knife edge about said axis while against said top of said cornea so as to scrape said cornea using said knife edge until said refractive error has been substantially corrected.

14. Apparatus of claim 13 including means to axially advance said blade incrementally against said cornea until said refractive error has been corrected.

15. Apparatus of claim 13 including indexing means to provide indication of the axial location of said profiling tool relative to said cornea.

16. Apparatus for correcting refractive error in an eye having a cornea with a center visual axis comprising:

a sharpened straight knife edge blade;

means to position said sharpened straight knife edge blade tangentially to and axially supported against an anterior surface of said cornea at said visual axis to axially rotatably scrape said cornea concentrically about said visual axis to remove corneal material and thereby substantially correct said refractive error.

17. An implement for surgically reprofiling the anterior surface of the cornea of an eye comprising:

a tool comprising a spindle having at one end thereof, constituting its inner end, a sharpened knife edge scraper blade means projecting endwise therefrom and extending outwardly from the spindle axis for scraping off portions of the anterior surface of the cornea by rotation or oscillation of the tool with the edge of the blade means in scraping engagement with said anterior surface;

means for holding the spindle for rotation on its axis and for axial movement with the spindle extending at its said inner end out of said holding means;

means for mounting said holding means on the cornea of an eye in fixed relation to the eye with the blade means at the inner end of the spindle in a position tangential to the anterior surface of the cornea at a center axis of said eye for scraping engagement with the anterior surface of the cornea to scrape said surface in a circular pattern;

and means for gauging the extension of the inner end of the spindle from the holding means to gauge the penetration of the edge of the blade means into the cornea for said scraping;

said gauging means being adjustable to vary the extension of the inner end of the spindle from the holding means.

18. An implement for surgically reshaping the anterior surface of the cornea of an eye comprising:

an axial tool having at one end thereof, constituting its inner end, a sharpened knife edge blade means projecting endwise therefrom and extending outwardly from the axis of the tool for correcting refractive error on the anterior surface of the cornea by rotation or oscillation of the tool with the edge of the blade means in tangential engagement with said anterior surface;

means for holding the tool for rotation on its axis and for controllable axial movement, with the tool extending, at its said inner end, out of said holding means;

means for mounting said holding means on the cornea of an eye in fixed relation to the eye with the blade means at the inner end of the tool in position for said tangential engagement with the anterior surface of the cornea;

and means for gauging and adjusting the axial extension of the inner end of the tool from the holding means to gauge the locus of the knife edge of the blade means relative to said anterior surface of said cornea.

19. Apparatus for correcting refractive error in an eye having a cornea with a visual axis, comprising:

a profiling tool, said tool having a sharpened straight knife edge blade to scrape said cornea to a desired corneal radius;

means to retain said knife edge blade of said profiling tool tangential to said cornea about said axis;

means to rotate or oscillate said tool about said axis so as to scrape said cornea with said knife edge until said refractive error has been substantially corrected; and means to incrementally advance or retract said tool axially along said axis.

20. Apparatus of claim 19 including means to axially advance said blade incrementally against said cornea until said refractive error has been corrected.

21. Apparatus of claim 19 including indexing means to provide indication of the axial location of said profiling tool relative to said cornea.

22. Apparatus of claim 19 wherein said knife edge blade is such to effectively increase the corneal radius.

23. Apparatus of claim 22 wherein said knife edge blade comprises a plurality of radial blades, the bottom sharpened knife edges of which are transverse to the axis of said profiling tool.

24. Apparatus of claim 19 wherein said knife edge blade is such to effectively decrease the corneal radius.

25. Apparatus of claim 24 wherein said knife edge blade comprises a plurality of radial blades, the bottom sharpened ends of which are concave relative to the axis of said profiling tool.

26. Apparatus of claim 19 wherein said means to retain said knife edge blade is substantially transparent.

* * * * *